(12) United States Patent
Mitchell

(10) Patent No.: US 10,675,170 B2
(45) Date of Patent: Jun. 9, 2020

(54) QUICK CLIP FOR A CLUB FOOT DEVICE

(71) Applicant: John R. Mitchell, Wayland, IA (US)

(72) Inventor: John R. Mitchell, Wayland, IA (US)

( * ) Notice: Subject to any disclaimer, the term of this patent is extended or adjusted under 35 U.S.C. 154(b) by 373 days.

(21) Appl. No.: 14/925,338

(22) Filed: Oct. 28, 2015

(65) Prior Publication Data

US 2016/0113803 A1 Apr. 28, 2016

Related U.S. Application Data

(60) Provisional application No. 62/069,637, filed on Oct. 28, 2014.

(51) Int. Cl.
*A61F 5/01* (2006.01)

(52) U.S. Cl.
CPC .......... *A61F 5/0193* (2013.01); *A61F 5/0116* (2013.01)

(58) Field of Classification Search
CPC .... A61F 5/0111; A61F 5/0116; A61F 5/0127; A61F 5/0193; A61F 5/01; A61F 5/0102; A61F 5/0113; A61F 5/0195; A61F 5/14

USPC ................... 602/29, 5, 23; 128/882
See application file for complete search history.

(56) References Cited

U.S. PATENT DOCUMENTS

| | | | |
|---|---|---|---|
| 2007/0142760 A1* | 6/2007 | Mitchell | A61F 5/0111 602/29 |
| 2008/0214975 A1* | 9/2008 | Mosler | A61F 5/0193 602/29 |
| 2011/0028876 A1* | 2/2011 | Mitchell | A61F 5/0193 602/24 |

* cited by examiner

*Primary Examiner* — Anna K Kinsaul
*Assistant Examiner* — Caitlin A Carreiro
(74) *Attorney, Agent, or Firm* — Nyemaster Goode, P.C.

(57) ABSTRACT

A system for connecting parts of a device used to treat club foot. An elongated member is attachable one or more mounting plates. The angle between the elongated member and the mounting plates can be varied by changing a channel of the mounting plates.

9 Claims, 3 Drawing Sheets

QUICK CLIP FOR A CLUB FOOT DEVICE

CROSS-REFERENCE TO RELATED APPLICATIONS

The present application claims priority to provisional patent application 62/069,637 which was filed on Oct. 28, 2014, and is hereby expressly incorporated by reference in its entirety.

BACKGROUND

Dr. Ignacio Ponseti is an internationally famous physician and surgeon specializing in the treatment and management of a childhood deformity commonly know as a club foot. Dr. Ponseti has for many decades promoted the use of a foot and ankle abduction device, or orthosis, that is used to correct and prevent relapses of the club foot deformity. These abduction devices typically consist of a rigid bar connected between shoes worn by the child which the bar separates the feet of the child and holds the feet in an outward rotation or abduction. Typically, if the condition is diagnosed early enough, this device is worn full-time for a period of months, but during the period of treatment, the angle of outward rotation is periodically adjusted.

The Ponseti technique, as it has become known throughout the world, has been highly successful in treating club feet without the necessity of corrective surgery. Many devices have been designed and used for many, many years in applying the Ponseti technique. Currently used devices that apply the Ponseti technique are shown in U.S. Pat. No. 7,267,657. In this patent, there are disclosed improvements in such devices which provide for quick release of the mounts from the abduction bar and universal mounts that can be attached to any shoe. The embodiments described herein are particularly useful in developing countries as the costs associated with the embodiments are less expensive to make and can be attached to any footwear.

SUMMARY OF THE INVENTION

The preferred embodiment contains an elongated member with means for attachment to a mounting plate that can be used for mounting a left footed and/or right footed shoe. The elongated member is preferably aluminum and the mounting plates are preferably a plastic. The elongated member attaches to the mounting plates via a movable insert captured by an opening in the elongated member. The mounting plates have openings in which screws or some other attachment means can be inserted. The attachment means are then attached to any shoe that a user may have.

DETAILED DESCRIPTION

Figure 1:
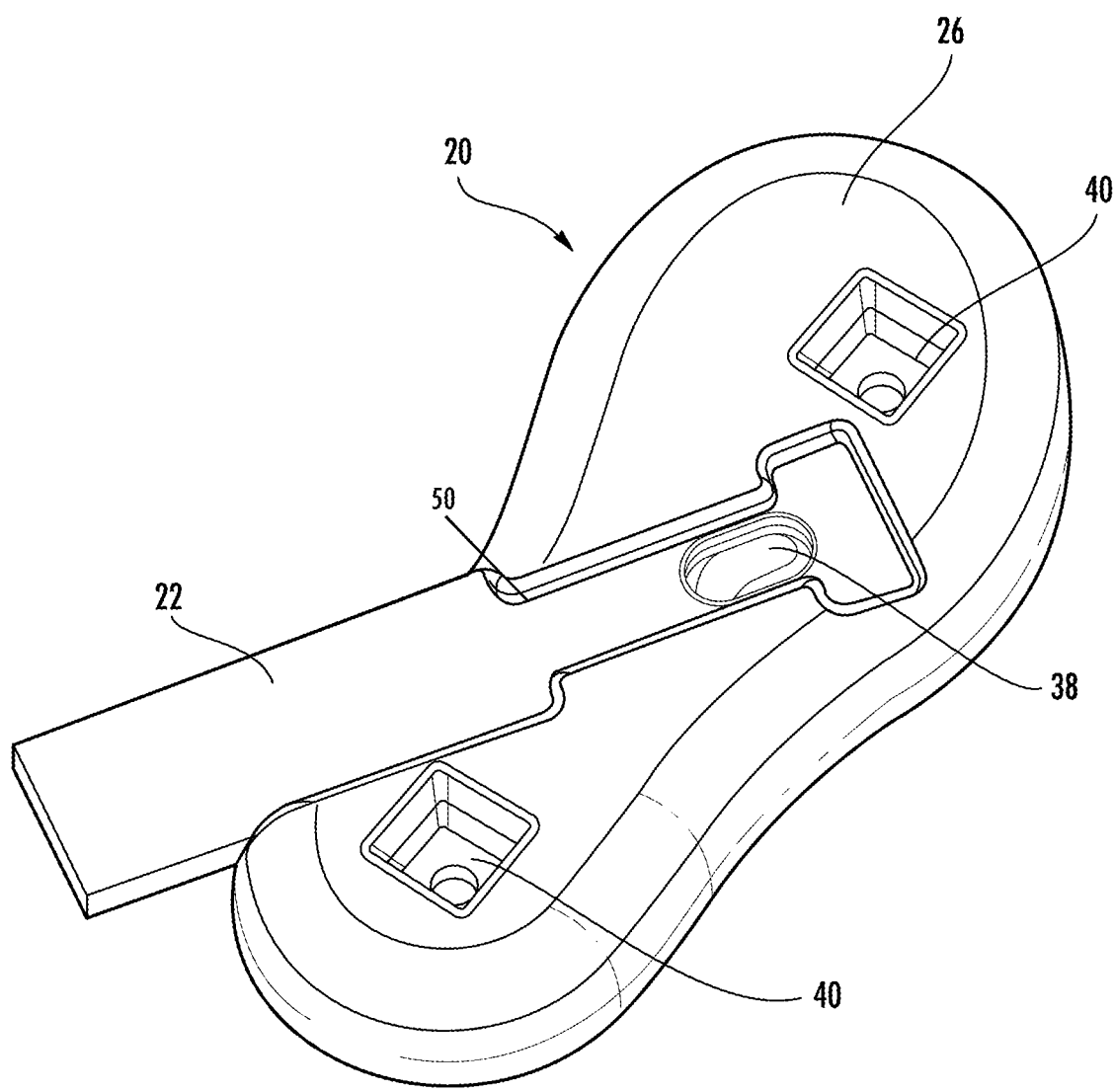
FIG. 1 is a perspective view of a mounting plate attached to an elongated member.
Figure 2:
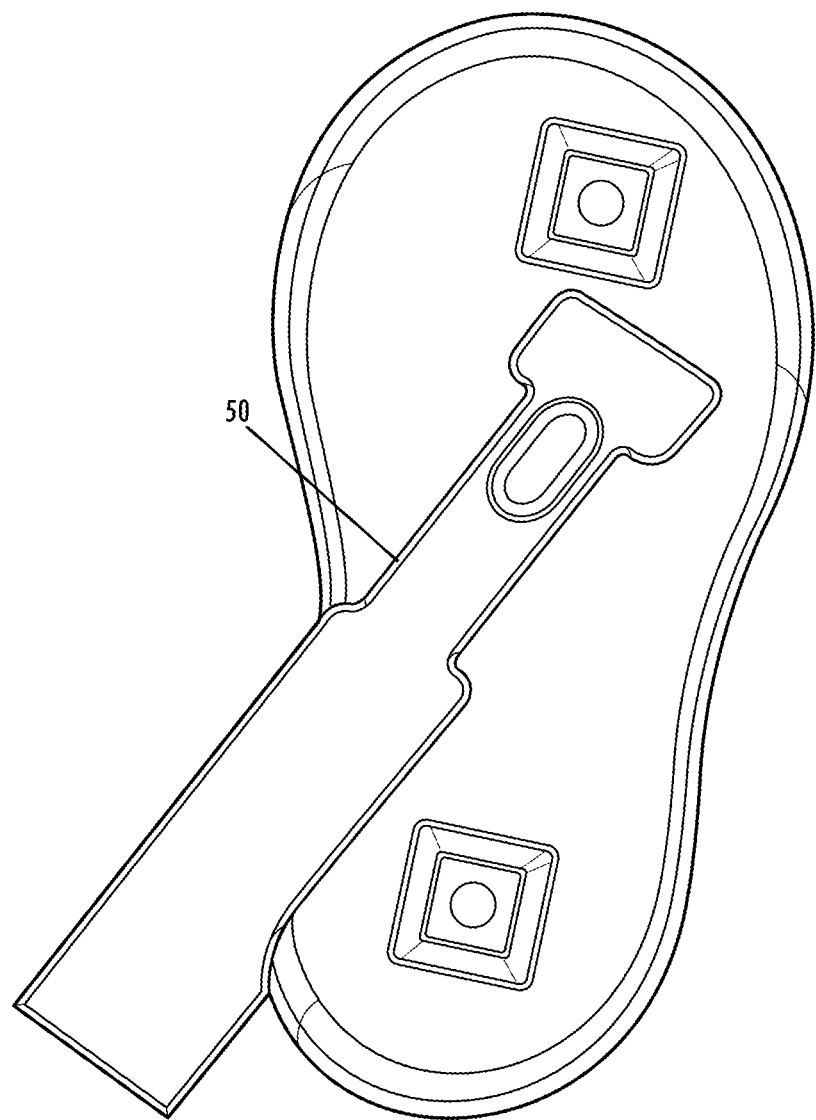
FIG. 2 is a top view of the mounting plate and elongated member.
Figure 3:
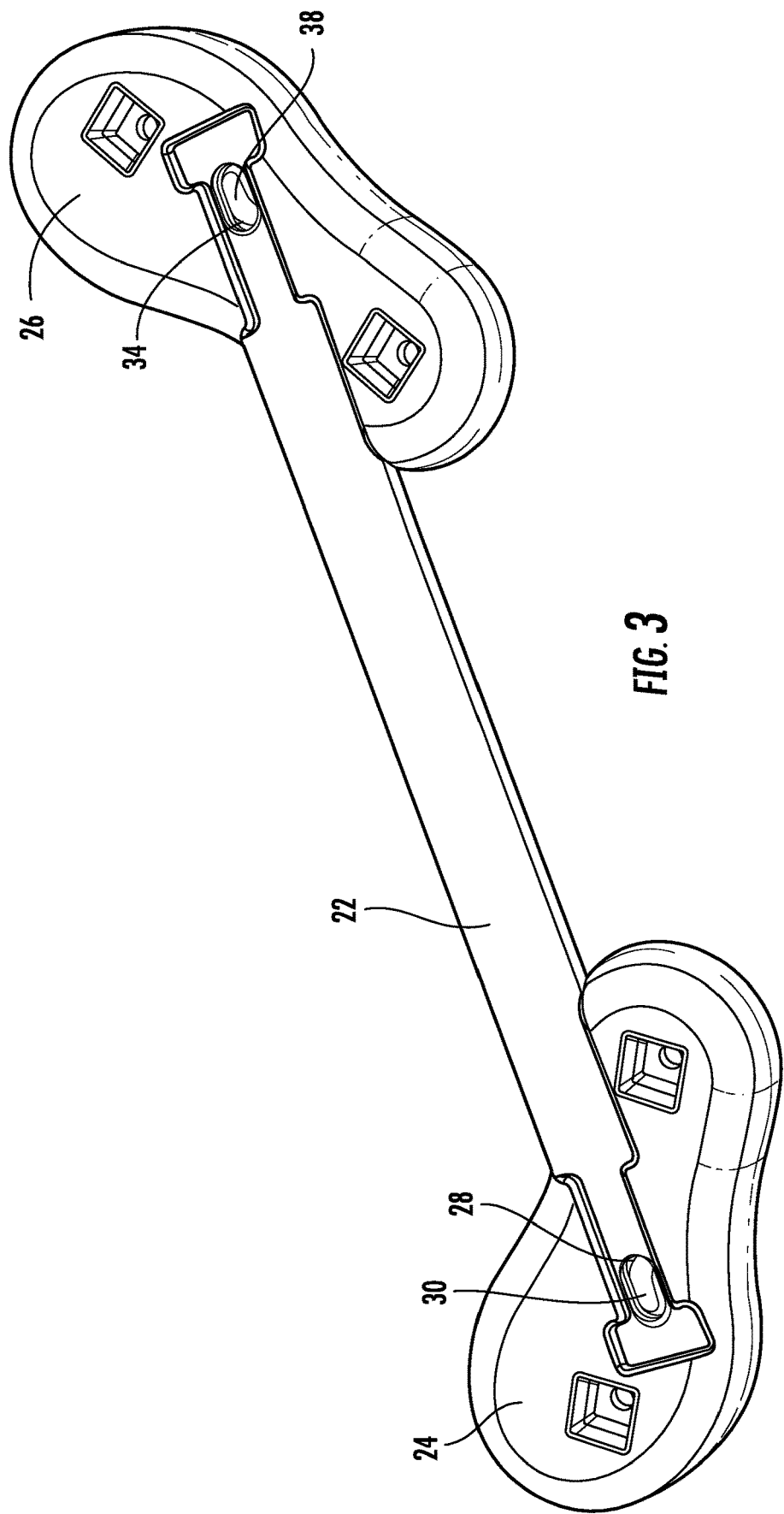
FIG. 3 is a perspective view of the invention showing the elongated member connected to two mounting plates.

Now referring to the drawings, FIGS. 1-3 show a connection system 20 comprising an elongated member 22 and universal mounting plates 24, 26. The elongated member 22 is preferably made of aluminum. The elongated ember 22 has an opening 28 sized to correspond to tab 30 on the mounting plate 24. Additionally, in FIG. 3, a second opening 34 in the elongated member 22 corresponds to a second tab 34 on the mounting plate 26. The tabs 30, 34 are flexible to allow movement without breaking. Although mounting plate 24 is shown in FIG. 4 as a left footed mounting plate, the plate 24 is constructed such that it can be inverted and used as a right footed mounting plate. The same is true for mounting plate 26 in that it can be used as a right or left footed mounting plate.

Each mounting plate 24, 26 have recesses 40 which allow the plates 24, 26 to be mounted to a shoe (not shown). Additionally, each plate 24, 26 has a channel 50 sized to accommodate the elongated member 22. The channel 50 is set at an angle such that a user's foot is positioned appropriately to treat club foot. In the preferred embodiment, the angle is sixty degrees for both feet. The angle can be varied depending on the specifics of the user. Additionally, the angle on the left mounting plate 24 may be the same or different than the angle on the right mounting plate 26. As the elongate member 22 is slid into the channel 50, eventually the tab 30 or 34 of the mounting plate 24 or 26 will flex and allow the elongate member 22 to slide over the tab 30 or 34. The tab 30 or 34 will then insert itself into opening 28 or 38. The process is repeated for the other side of the elongated member 22 on the remaining plate. In order to unsecure the elongated member 22, the tab 30 or 34 is pushed and the elongated member 22 is slid out from the plate.

What is claimed is:

1. A system for connecting parts of a device to correct club foot, comprising:
    an elongated member having a first end and a second end;
    a first mounting plate;
    the first mounting plate configured to accommodate a left shoe of a user;
    wherein the first mounting plate is configured to be directly mounted to the left shoe of a user;
    the first mounting plate comprising a flexible tab;
    the elongated member having an opening;
    the tab selectively insertable into the opening;
    a channel in the first mounting plate;
    the channel having a shape corresponding to a shape of the first end of the elongated member;
    the flexible tab within the channel;
    a plurality of recesses in the first mounting plate;
    the plurality of recesses configured to attach to the left shoe of a user;
    the first mounting plate can be inverted;
    wherein the inverted first mounting plate is configured to accommodate a right shoe of a user.

2. The system of claim 1, wherein:
    the elongated member is made of metal.

3. The system of claim 2, wherein:
    the first mounting plate is made of a plastic.

4. The system of claim 1 further comprising:
    a second mounting plate;
    wherein the second mounting plate can be used for either a user's left or right foot;
    wherein when the first mounting plate is inverted to accommodate a right shoe of a user, the right shoe will be located above the elongated member and the left shoe will also be located above the elongated member.

5. The system of claim 1, wherein:
    the first mounting plate can be used for either a user's left or right foot.

6. A universal mounting plate, comprising:
a channel;
a flexible tab;
wherein the tab can flex from a first position to a second position;
wherein the universal mounting plate can be used for a user's left or right foot;
the universal mounting plate configured to accommodate a left shoe of a user;
wherein the universal mounting plate is configured to be directly mounted to the left shoe of a user;
a plurality of recesses in the universal mounting plate;
the plurality of recesses configured to attach to the left shoe of a user;
the universal mounting plate can be inverted;
wherein the inverted universal mounting plate is configured to accommodate a right shoe of a user;
wherein when the universal mounting plate is inverted to accommodate a right shoe of a user, the inverted universal mounting plate is configured to have a combination of shoes in the same orientation.

7. The universal mounting plate of claim 6, further comprising:
an attachment mechanism configured such that the universal mounting plate can be directly selectively attached to a shoe.

8. The universal mounting plate of claim 7, wherein:
the universal mounting plate is made of a plastic.

9. The universal mounting plate of claim 8, wherein:
the tab is within the channel.

* * * * *